(12) United States Patent
Moller

(10) Patent No.: US 9,101,722 B2
(45) Date of Patent: Aug. 11, 2015

(54) DOSE SETTING MECHANISM FOR AN INJECTION DEVICE CAPABLE OF PRESETTING A MAXIMUM DOSE

(75) Inventor: Claus Schmidt Moller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 399 days.

(21) Appl. No.: 11/816,918

(22) PCT Filed: Feb. 24, 2006

(86) PCT No.: PCT/EP2006/001707
§ 371 (c)(1),
(2), (4) Date: Jan. 3, 2008

(87) PCT Pub. No.: WO2006/089767
PCT Pub. Date: Aug. 31, 2006

(65) Prior Publication Data
US 2008/0154211 A1   Jun. 26, 2008

(30) Foreign Application Priority Data

Feb. 28, 2005   (EP) .................................. 05075475

(51) Int. Cl.
*A61M 5/315*   (2006.01)

(52) U.S. Cl.
CPC ....... *A61M 5/31536* (2013.01); *A61M 5/31535* (2013.01); *A61M 5/31543* (2013.01); *A61M 5/3158* (2013.01); *A61M 5/31551* (2013.01); *A61M 2005/3154* (2013.01)

(58) Field of Classification Search
CPC .............. A61M 5/24; A61M 5/31535; A61M 5/31551; A61M 5/3158; A61M 5/31593; A61M 5/31543; A61M 5/31585; A61M 2005/2488; A61M 5/31548; A61M 5/3155; A61M 5/31573; A61M 5/31578; A61M 5/31583; A61M 5/31591; A61M 5/31536; A61M 2005/3154

USPC .................................. 604/186, 207–211, 246
See application file for complete search history.

(56) References Cited

U.S. PATENT DOCUMENTS

| 5,092,842 A | 3/1992 | Bechtold et al. |
| 5,104,380 A | 4/1992 | Holman et al. |

(Continued)

FOREIGN PATENT DOCUMENTS

| DE | 19838760 | 4/2000 |
| DE | 19900792 | 6/2000 |

(Continued)

OTHER PUBLICATIONS

European Search Report issued in connection with counterpart EP Application No. 05075475.3-2310, mailed Dec. 15, 2005.

(Continued)

*Primary Examiner* — Theodore Stigell
*Assistant Examiner* — Lauren M Peng
(74) *Attorney, Agent, or Firm* — Wesley Nicolas

(57) ABSTRACT

A dose setting mechanism for an injection device having a rotatably operated dose setting member, a presetting member being operable to limit the maximum dose settable by the dose setting member, and a first stopping member is operatively connected to the presetting member where the position of the first stopping member indicates the preset maximum dose. The first stopping member is adapted to rotatably engage with a second stopping member when the preset maximum dose has been set, thereby preventing setting of a further dose. The first and/or the second stopping member is/are movable along with the dose setting member, the first and second stopping members thereby being moved into engagement when a dose is set. Thereby a dose can be preset and the preset dose can easily be repeatedly set while ensuring an accurate dosage. Helps persons being visually impaired or having poor dexterity in setting a correct and accurate dose.

6 Claims, 6 Drawing Sheets

(56) References Cited

U.S. PATENT DOCUMENTS

| | | |
|---|---|---|
| 5,308,340 A | 5/1994 | Harris |
| 5,591,136 A | 1/1997 | Gabriel |
| 5,827,232 A * | 10/1998 | Chanoch et al. ............. 604/208 |
| 5,938,642 A | 8/1999 | Burroughs et al. |
| 6,193,698 B1 | 2/2001 | Kirchhofer et al. |
| 6,228,067 B1 | 5/2001 | Gabriel |
| 6,666,849 B1 * | 12/2003 | Marshall et al. ............. 604/246 |
| 7,195,616 B2 * | 3/2007 | Diller et al. ................. 604/224 |
| 7,196,616 B2 | 3/2007 | Huang |
| 2004/0059299 A1 * | 3/2004 | Moller ........................ 604/207 |
| 2004/0097883 A1 * | 5/2004 | Roe ............................... 604/207 |
| 2005/0261634 A1 * | 11/2005 | Karlsson .................... 604/197 |
| 2008/0262437 A1 | 10/2008 | Hirschel et al. |

FOREIGN PATENT DOCUMENTS

| | | |
|---|---|---|
| DE | 102005044096 A1 | 11/2006 |
| EP | 268191 | 11/1987 |
| EP | 713403 | 2/1995 |
| EP | 744975 | 8/1995 |
| EP | 831947 | 10/1997 |
| EP | 0937471 A2 | 8/1999 |
| EP | 0937471 A3 | 8/1999 |
| EP | 0937471 B1 | 8/1999 |
| EP | 1855743 | 8/2006 |
| EP | 5796880 | 8/2007 |
| JP | 05082441 B2 | 4/1993 |
| JP | H11216181 A | 8/1999 |
| WO | WO 99/64092 | 12/1999 |
| WO | WO 01/19434 | 3/2001 |
| WO | WO 01/54757 | 8/2001 |
| WO | WO 03/011374 | 2/2003 |
| WO | WO 03/053499 | 7/2003 |

OTHER PUBLICATIONS

International Search Report issued in connection with counterpart PCT Application No. PCT/EP2006/001707, mailed May 15, 2006.
Written Opinion issued in connection with counterpart PCT Application No. PCT/EP2006/001707, mailed Sep. 20, 2007.
Public Use of "AutoPen 24".

* cited by examiner

DOSE SETTING MECHANISM FOR AN INJECTION DEVICE CAPABLE OF PRESETTING A MAXIMUM DOSE

CROSS-REFERENCE TO RELATED APPLICATIONS

This application is a 35 U.S.C. §371 national stage application of International Patent Application PCT/EP2006/001707 (published as WO 2006/089767 A1), filed Feb. 24, 2006, which claims priority of European Patent Application 05075475.3, filed Feb. 28, 2005; this application further claims priority under 35 U.S.C. §119 of U.S. Provisional Application 60/657,854, filed Mar. 2, 2005.

FIELD OF THE INVENTION

The present invention relates to a dose setting mechanism for an injection device, preferably of the kind being suitable for repetitive self-injection of medication, e.g. of insulin or growth hormone, the dose setting mechanism making it easy for a user to set a predetermined dose. Furthermore, the present invention relates to an injection device having such a dose setting mechanism.

BACKGROUND OF THE INVENTION

When drugs are to be injected into the human body, it is often essential that the dose to be injected is set with high precision, as a too high or too low dose can have undesired consequences. However, for persons being visually impaired or having poor dexterity it may be difficult to set the desired dose. Accordingly, it is desirable to provide an injection device with a preset mechanism which aids such persons in the process of setting a dose.

One such device is described in U.S. Pat. No. 6,228,067 disclosing an injection device having a movable expressing member for expressing an injection fluid from a fluid container. An actuating member is used for displacing the expressing member. Between the actuating member and the expressing member, a position-dependent connecting device is provided, which is disabled in a distal end position of the actuating member and is enabled in a position range adjacent to the distal end position of the actuating member, including a proximal end position. Thereby an injection device is obtained which is adapted to permit a patient to repeatedly administer the same constant injection dose. The preset dose is set by pulling the actuating member out until this movement is stopped by means of the connecting device. Subsequently the set dose is injected by pressing the actuating member. Thus, the preset mechanism has been applied to an injection device in which the dose setting as well as the injection is performed by means of linear movements. This is a disadvantage because setting and/or injecting a dose of one international unit corresponds to a very small movement of the actuating member, and it is therefore difficult to set and/or inject an accurate dose. Accordingly, it is also difficult to set the preset dose accurately and thereby to ensure subsequent accurate dosage. This is particularly disadvantageous because a too high or too low preset dose will result in a too high or too low dose being set each time the preset dose is set, and the accumulated dose over a longer period in time will therefore deviate substantially from what was intended.

U.S. Pat. No. 5,308,340 discloses a multiple dose injection pen comprising a follower which can be adjusted to any position along threads adapted to engage with internal threads of a dose knob. The principle function of the follower is to set a maximum allowable dose where the syringe is going to be used by persons who may have difficulty remembering the proper dosage. The follower limits the axial movement of the dose knob during setting of a dose, since the follower will abut a collar of the dose knob when the maximum dosage has been set. The follower and the collar are moved linearly into abutment.

EP 0 937 471 discloses a medication delivery pen having a repeat-dose feature that limits motion of the dose control mechanism using an adjustable repeat-dose stop on the dose knob. The pen comprises an adjustable dose stop which prevents axial movement of the dose knob beyond a set desired dose. When the desired dose has been set, a proximal face of the dose stop comes into contact with a distal face on a clicker, thereby preventing further axial movement of the dose knob. The faces are moved linearly into contact.

SUMMARY OF THE INVENTION

It is, thus, an object of the present invention to provide a dose setting mechanism having a preset mechanism which can be set more accurately than prior art preset mechanisms.

It is a further object of the present invention to provide a preset mechanism for a dose setting mechanism in which the dose can be set in an accurate manner.

It is an even further object of the present invention to provide an injection device in which a desired dose may easily and accurately be repeatedly set.

According to a first aspect of the present invention the above and other objects are fulfilled by providing a dose setting mechanism for an injection device, the dose setting mechanism comprising:
  a dose setting member being rotatably operable by a user to set a desired dose,
  a presetting member being operable to limit the maximum dose settable by the dose setting member,
  a first stopping member being operatively connected to the presetting member in such a manner that the position of the first stopping member is changed when the presetting member is operated, the position of the first stopping member thereby being indicative of the preset maximum settable dose,
  a second stopping member being adapted to engage with the first stopping member in such a way that when the first stopping member and the second stopping member engage, the dose setting member can not be operated to set a further dose,
wherein the first and/or the second stopping member is/are movable along with the dose setting member during setting of a dose, said movement causing the first and the second stopping member to perform a rotational movement relatively to each other, said relative rotational movement causing the first and the second stopping member to engage when the maximum settable dose has been set, thereby preventing further setting of a dose.

In the present context the term 'dose setting mechanism' should be interpreted to mean a part of an injection device which is used for setting a dose to be injected by means of the injection device. The injection device is preferably of the kind being suitable for repetitive self-injections of medication, such as insulin or growth hormone. The injection device is of the kind where the dose setting as well as the injection is performed by means of rotating movements. In such injection devices the dose setting as well as the injection of the set dose is much more accurate than dose setting and injection in injection devices where these functions are performed linearly. This is because the rotational movements provide a longer path to be traveled by the involved components when setting or injecting a dose of one international unit. In addition to the rotational movement, the dose setting member may perform a translational movement, the resulting movement of the dose setting member thereby being a spiral movement.

The dose setting member is a part of the dose setting mechanism which can be rotatably operated by the user in order to set a desired dose. The dose setting member could, thus, be or comprise a rotatable dose knob or another mechanism which is normally used for this purpose in injection devices of the kind mentioned above.

The presetting member is operable to limit the maximum dose settable. Thus, the presetting member can be operated so as to set a 'maximum dose'. When a maximum dose has been set by means of the presetting member, this dose may be set repeatedly by the user merely by operating the dose setting member to the maximum dose each time a dose is to be set. This makes it easier for persons being visually impaired or having poor dexterity, or for children, to set a correct dose. Furthermore, the preset limit can easily be changed in case the dose needs to be changed.

The first stopping member is operatively connected to the presetting member. Thus, when the presetting member is operated by a user, the first stopping member is moved accordingly, i.e. the position of the first stopping member is changed in accordance with the presetting of the maximum dose settable. Thus, the position of the first stopping member is indicative of the preset maximum dose. The first stopping member may be or form part of the presetting member. Alternatively, the first stopping member may be connected to the presetting member in a mechanical or electronical manner, or in any other suitable manner as long as the operation of the presetting member causes the first stopping member to move.

When a dose is set by rotating the dose setting member, the first and/or second stopping member is moved along with the dose setting member. This movement causes the distance between the first stopping member and the second stopping member to decrease in such a way that when the position of the first stopping member coincides with the position of the second stopping member, the first and second stopping members thereby engaging each other, the maximum dose settable has been set. The engagement of the first and second stopping members thereby has the effect that a further dose can not be set, i.e. it is not possible to set a dose which exceeds the preset maximum dose. It is of no importance whether it is the first stopping member, the second stopping member or both which is/are moved along with the dose setting member as long as the movement causes a decrease in the distance between the first stopping member and the second stopping member as described above.

In the present context the term 'movable along with the dose setting member' should not be interpreted narrowly as 'performing the same movement as the dose setting member'. Rather, the stopping member(s) is/are caused to move when the dose setting member is rotated to set a dose, and the kind of movement or the direction of movement need not be the same as the physical movement of the dose setting member. What is important is, that the first stopping member and the second stopping member are caused to perform a rotational movement relatively to each other when the dose setting member is rotated to set a dose, and that this relative rotational movement causes the distance between the first stopping member and the second stopping member to decrease in such a way that when the preset maximum dose has been set by the dose setting member, the first stopping member and the second stopping member engage, thereby preventing setting of a further dose. Thus, during the setting of a dose the distance between the first stopping member and the second stopping member in effect indicates how much further dose can be set before the preset maximum dose has been set.

It is an advantage that the first and second stopping member are moved into engagement by means of a relative rotational movement, because the relative rotational movement provides a more accurate definition of the point where the maximum settable dose has been reached, than it is the case for a relative linear movement.

In the present context the term 'distance' should be broadly interpreted. Thus, the distance could, e.g., be an angular and/or an axial distance.

Thus, according to the present invention a preset mechanism has been applied to a device in which the dose setting as well as the injection is performed by means of rotating movements, the dosage thereby being provided in a very accurate manner. Accordingly, the dose setting mechanism of the present invention combines an accurate dose setting with a preset mechanism, thereby providing accurate dosage, also for persons being visually impaired or having poor dexterity.

The first and/or the second stopping member may rotate along with the dose setting member during setting of a dose. Alternatively or additionally, the first and/or the second stopping member may perform a translational movement, e.g. along a longitudinal axis of the injection device.

In one embodiment the first stopping member is movable along with the dose setting member during setting of a dose, the second stopping member being at least substantially fixed relatively to a housing of the injection device. In this embodiment the second stopping member remains at least substantially fixed relatively to the housing while the first stopping member is movable along with the presetting member during presetting of the maximum dose as well as along with the dose setting member during setting of a dose. Alternatively, the first stopping member may remain at least substantially fixed relatively to the housing during the setting of a dose in which case only the second stopping member is moved along with the dose setting member. Alternatively, the first stopping member as well as the second stopping member may be movable along with the dose setting member during setting of a dose. This has already been described above.

The first stopping member and the second stopping member may each comprise at least one stopping surface, the stopping surfaces of the first and second stopping members being adapted to abut each other when the maximum settable dose has been set, thereby preventing further relative rotational movement between the first and the second stopping member. In this embodiment the first and/or the second stopping member perform(s) a rotational movement during setting of a dose. At least one of the first and second stopping members may further perform a translational movement, the resulting movement of at least one of the stopping members thereby being a spiral movement. In any event the movement is performed until the stopping surfaces abut, thereby preventing further mutual rotational movement. This, in turn, prevents further setting of a dose.

The first stopping member and the second stopping member may each comprise a plurality of teeth, the number of teeth on each stopping member corresponding to the number of unit doses being set when the dose setting member is rotated through one revolution. In this embodiment a spiral movement of at least one of the first and second stopping members during setting of a dose is necessary in order to allow relative rotation during setting of a dose up until the maximum dose, and in order to prevent further relative rotation when the maximum dose has been set. When the number of teeth on each stopping member corresponds to the number of unit doses per revolution, it is ensured that setting of a further dose is prevented exactly when the preset dose has been set, i.e. it is not possible to set a dose which is a few units higher than the preset dose. This even further improves the accuracy of the presetting mechanism.

According to a second aspect of the present invention the above and other objects are fulfilled by providing an injection device comprising a dose setting mechanism according to the first aspect of the present invention. The injection device may be of the kind which is suitable for repetitive self-injection of medication, such as insulin or growth hormone. Preferably, the injection device has an elongated shape, i.e. it is preferably of a pen-shaped type.

BRIEF DESCRIPTION OF THE DRAWINGS

The invention will now be further described with reference to the accompanying drawings, in which.

DETAILED DESCRIPTION OF THE DRAWINGS

Figure 1:
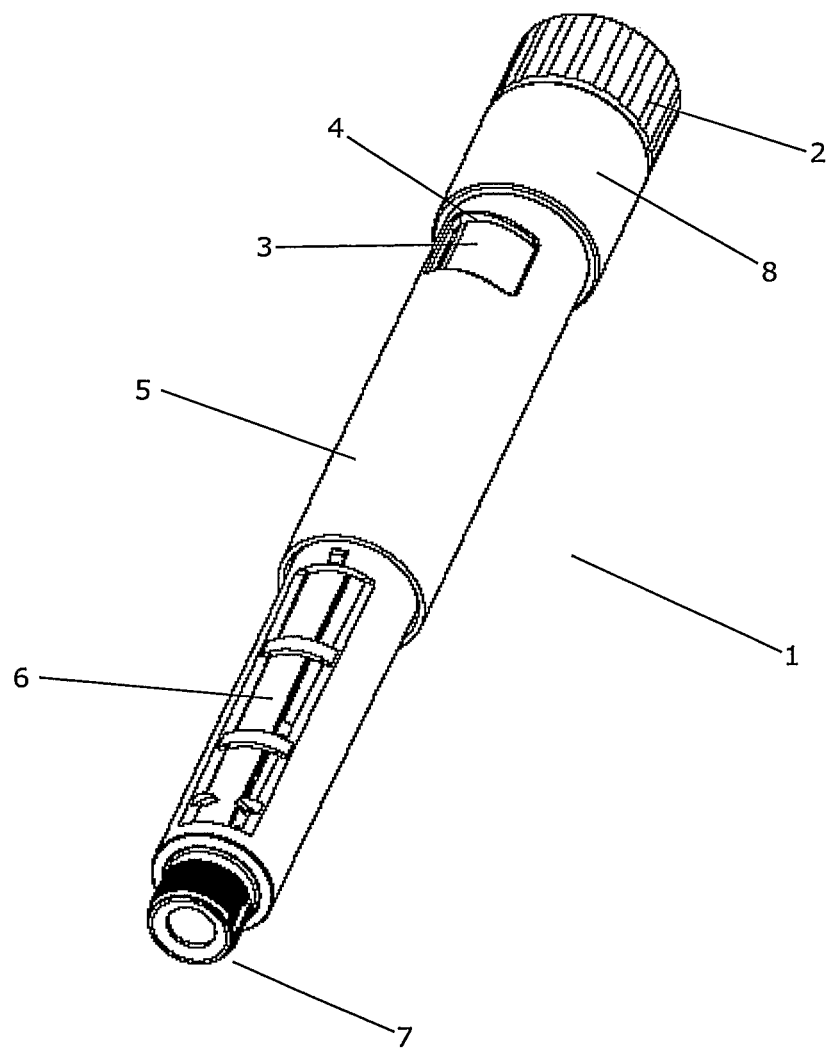
FIG. 1 is a perspective view of an injection device with a dose setting mechanism according to an embodiment of the present invention.

FIG. 1 is a perspective view of an injection device 1 having a dose setting mechanism according to an embodiment of the present invention. The dose setting mechanism is operated by means of a dose setting member 2. When a dose is set the dose setting member 2 is rotated, thereby causing a scale drum 3 to be rotated as well. The rotational movement also results in an axial movement of the dose setting member 2 and the scale drum 3 in an outward direction. The scale drum 3 is visible through a window 4 in a housing 5 of the injection device 1. Thereby it is possible for a user to read the set dose by means of numbers written on the scale drum 3. The injection device 1 further comprises a compartment 6 adapted to accommodate a cartridge containing a fluid to be injected by means of the injection device 1. At the end 7 positioned opposite the dose setting member 2 it is possible to attach an injection needle. Finally, the dose setting mechanism comprises a presetting member 8 which is rotatable in order to preset a desired maximum dose.

Figure 2:
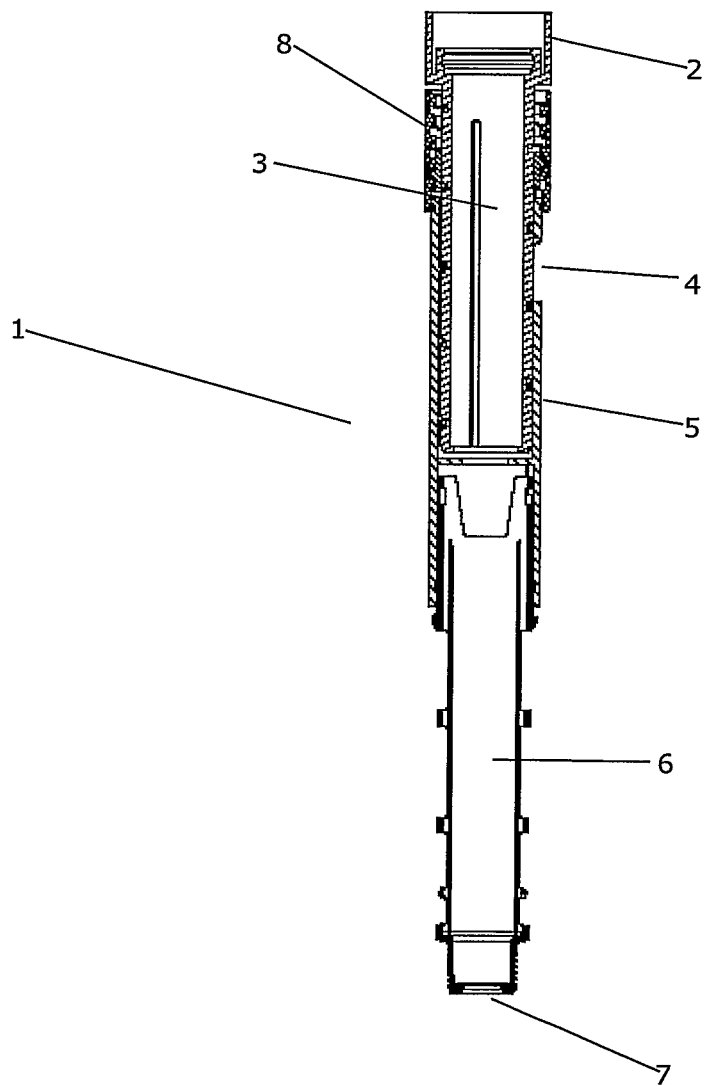
FIG. 2 is a side view of the injection device of FIG. 1 with parts broken away.

FIG. 2 is a side view of the injection device 1 of FIG. 1. Part of the housing 5 has been broken away, thereby revealing the position of the scale drum 3 inside the housing 5. The dose setting member 2 is positioned adjacent to the presetting member 8, i.e. a dose has not been set.

Figure 3:
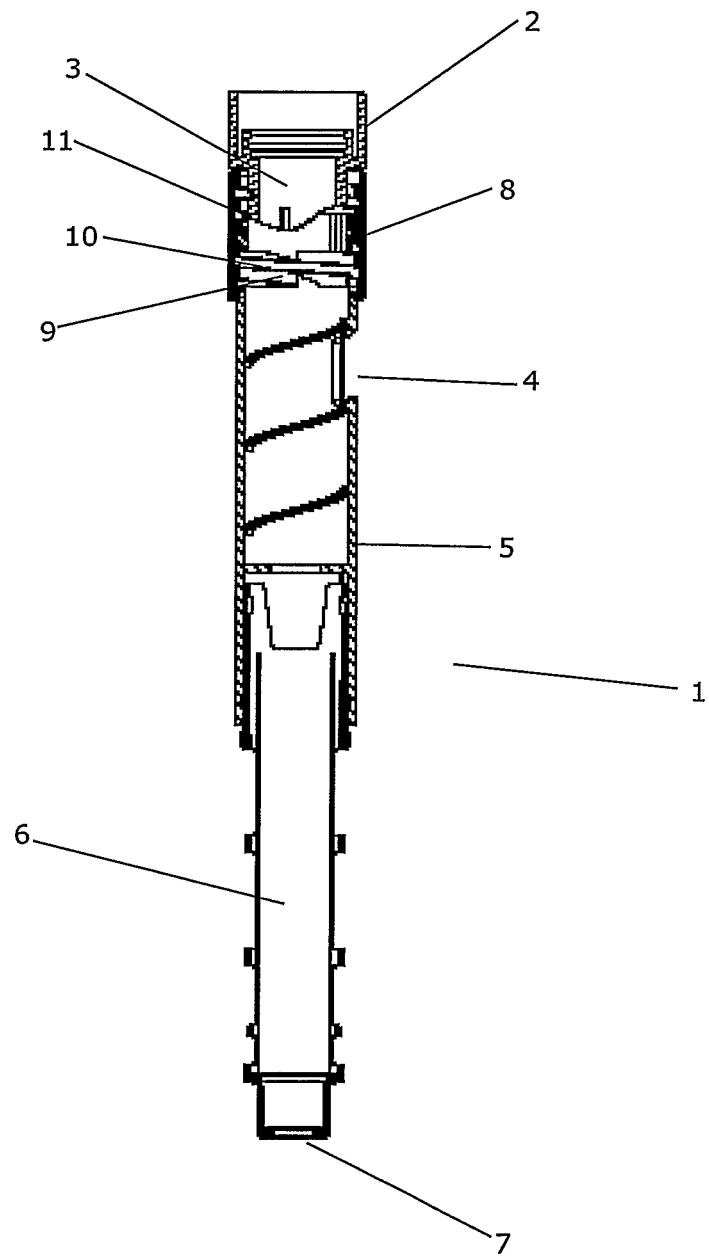
FIG. 3 is a cross sectional view of the injection device of FIG. 1, where the presetting member has been set to a maximum dose.

FIG. 3 is a cross sectional view of the injection device 1 of FIG. 1. However, part of the scale drum 3 is still visible. In FIG. 3 a first stopping member 9 is shown. The first stopping member 9 is operatively connected to the presetting member 8 by means of a thread 10 on the first stopping member 9 and a corresponding inner thread 11 on the presetting member 8. Thus, when the presetting member 8 is rotated the first stopping member 9 performs a spiral movement, and the resulting position of the first stopping member 9 will be indicative of the preset maximum settable dose. In FIG. 3 the presetting member 8 has been set to a non-zero maximum dose.

Figure 4:
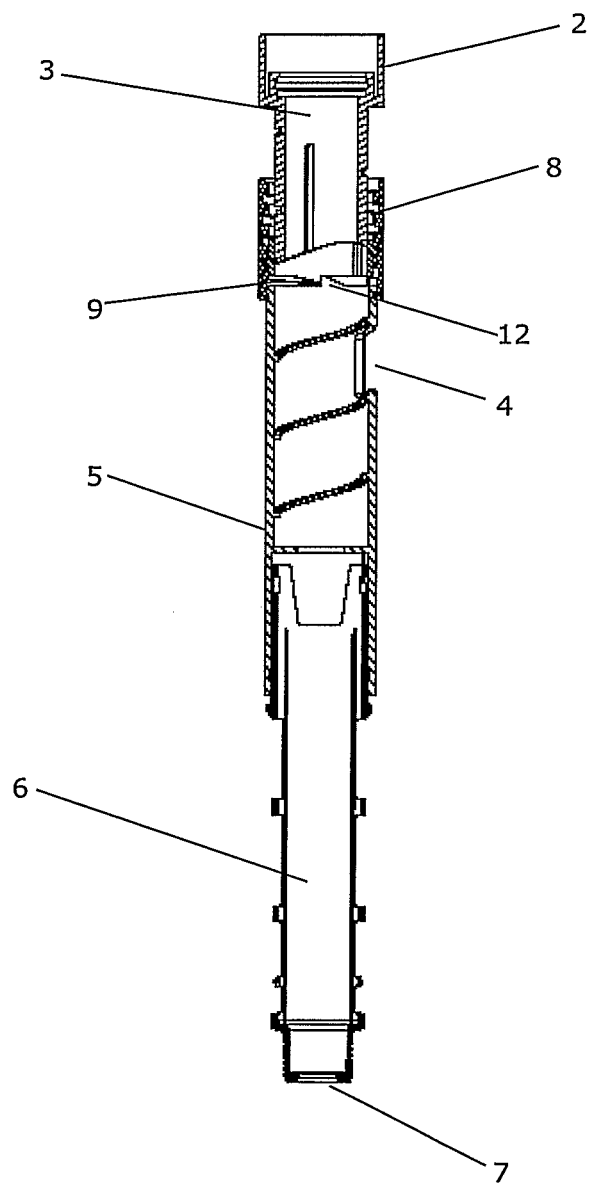
FIG. 4 is a cross sectional view of the injection device of FIG. 1 where a maximum dose has been set by means of the dose setting mechanism.

FIG. 4 is also a cross sectional view of the injection device 1 of FIG. 1. In FIG. 4 a second stopping member 12 in the form of a tooth present on the housing 5 is visible. The first stopping member 9 abuts the second stopping member 12, thereby indicating that the dose set is the maximum settable dose, i.e. it is not possible to set a further dose.

Figure 5:
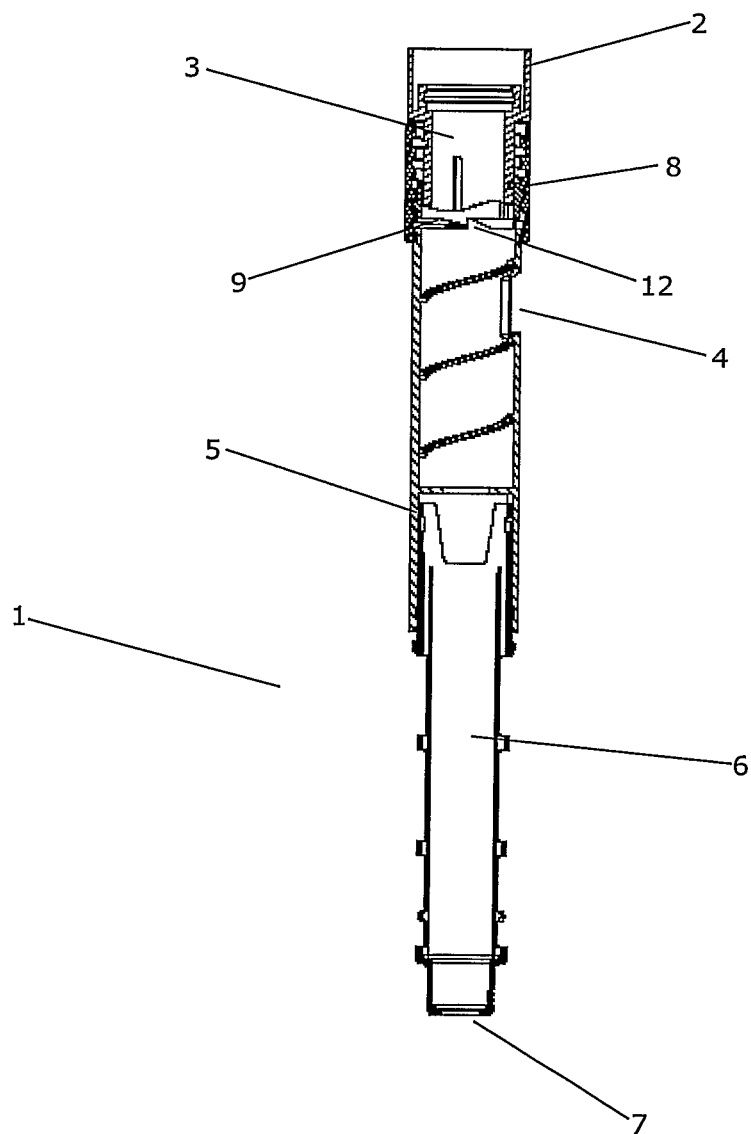
FIG. 5 is a cross sectional view of the injection device of FIG. 1, where the presetting member has been set to a maximum dose of 0 units.

FIG. 5 is also a cross sectional view of the injection device 1 of FIG. 1. In this case the presetting member 8 has been preset to a maximum settable dose of 0 units. This can be seen because the first stopping member 9 and the second stopping member 12 abut each other, and the dose setting member 2 is in the 'zero position', i.e. it has not been dialled away from the presetting member 8. Such a setting may, e.g., be used in case it is desired to prevent that a dose is accidentally set.

Figure 6:
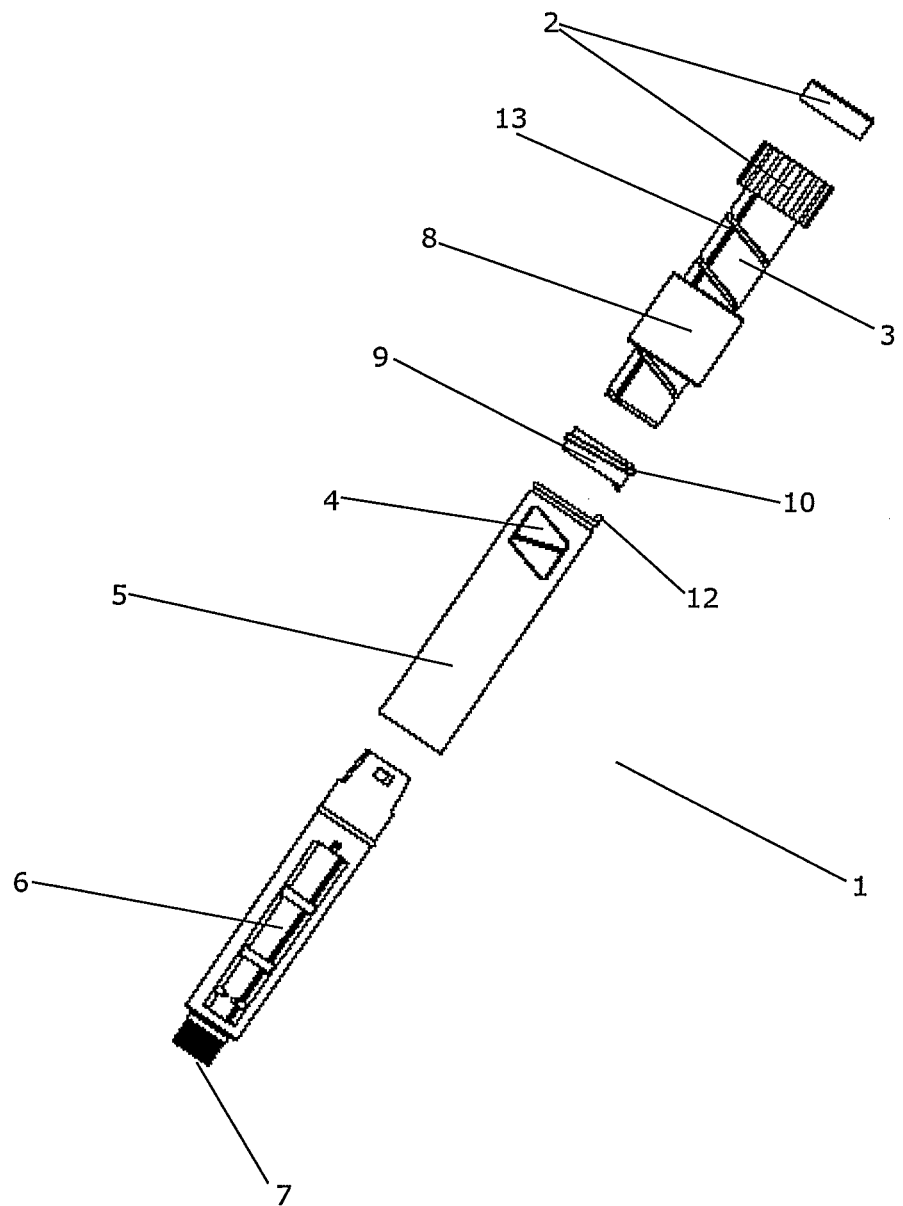
FIG. 6 is an exploded view of the injection device of FIG. 1.

FIG. 6 is an exploded view of the injection device 1 of FIG. 1. In this Figure the shapes of the various parts are clearly visible.

It should be noted that, for the sake of clarity, only one tooth is shown on first stopping member 9 and on the second stopping member 12. However, it should be understood that additional teeth may be present on the respective stopping members 9, 12, preferably the number of teeth on each stopping member 9, 12 corresponds to the number of unit doses being set when the dose setting member 2 is rotated through one revolution.

The stopping member 9 comprises an inner key (not shown) which engages an outer groove 13 on the scale drum 3. During setting of a maximum settable dose, the stopping member 9 is thereby moved along this outer groove 13 by means of a key-groove connection.

The injection device 1 shown in FIGS. 1-6 is preferably operated in the following manner. When it is desired to preset a maximum settable dose, the dose setting mechanism is initially operated to set this dose by rotating the dose setting member 2 in a manner normal for this kind of injection device 1. Once the desired dose is set the presetting member 8 is rotated until the first stopping member 9 (connected to the presetting member 8) abuts the second stopping member 12 (fixed to the housing 5). Thereby the presetting member 8 has been set to the desired maximum settable dose. When the set dose is subsequently injected by pressing the dose setting member 2 (and along with it the scale drum 3) back towards the housing 5, the first stopping member 9 will be forced to perform a translational movement away from the second stopping member 12. Thereby the first stopping member 9 and the second stopping member 12 no longer abut each other. The distance traveled by the first stopping member 9 is indicative of the dose being injected, i.e. the maximum settable dose. Accordingly, the resulting position of the first stopping member 9 is indicative of the preset maximum dose. The next time a dose is to be set, the dose setting member 2 is rotated in the usual manner. The first stopping member 9 will be forced to rotate and to translate in a direction towards the second stopping member 12. Thereby the dose setting member 2 can only be rotated until the preset maximum dose has been set, because when this is the case, the first stopping member 9 will again be in the position where it abuts the second stopping member 12, and a further dose can not be set. Thereby the preset maximum dose can be repeatedly set and injected until it is desired to change the dose. Then a new preset value is simply selected as described above.

The invention claimed is:

1. A dose setting device for setting the dose in an injection pen apparatus which has a housing, the dose setting device comprising:
a dose setting member that is rotatable by a user during a dose setting operation to set a dose, the dose setting member performing a spiral translation motion relative to the housing when rotated during dose setting and an opposite spiral translational motion during injection of the set dose such that the dose setting member returns to its original pre-dose setting position upon completion of ejecting of medication during the injection;
a presetting member being operable to limit a maximum size of a set dose, the presetting member being rotatably and non-axially disposed on the housing between a distal and a proximal end of the housing, the presetting member being rotatable relative to the housing to set a maximum dose size, and the presetting member remaining rotatably disposed on the housing between the distal and proximal ends during presetting of the limit of the maximum dose size, which is accomplished by rotating the presetting member;
a first stopping member coupled to the presetting member, wherein rotation of the presetting member results in a change in position of the first stopping member such that a user can preset a maximum dose size;
a second stopping member that engages with the first stopping member and, when the first and second stopping members are engaged, the stopping members prevent rotation of the dose setting member in a direction that would allow the user to set a dose that is larger than the maximum preset dose which was set by the presetting member, and wherein a rotational force applied by and between the first and second stopping members as a result of their rotational abutment with each other during the setting of a dose via the dose setting member does not result in rotation of the presetting member and thus does not change the size of the maximum preset dose;
wherein the first stopping member is moveable along with the dose setting member during the setting of a dose, the movement causing the first and second stopping members to perform a rotational movement relative to each other, the relative rotational movement causing the first and second stopping members to engage when the maximum settable dose has been reached during dose setting via the dose setting member, the maximum settable dose being one set by rotating the presetting member, wherein the first and second members engage rotationally and not axially during dose setting when the dose setting member is rotated and wherein during dose setting the angular distance between the first and second stopping members decreases until they engage.

2. A dose setting device for setting the dose in an injection pen apparatus which has a housing, the dose setting device comprising:
a dose setting member that is rotatable by a user during a dose setting operation to set a dose, the dose setting member performing a spiral translation motion relative to the housing when rotated during dose setting and an opposite spiral translational motion during injection of the set dose such that the dose setting member returns to its original pre-dose setting position upon completion of ejecting of medication during the injection;
a presetting member being operable to limit a maximum size of a set dose, the presetting member being rotatably and non-axially disposed on the housing between a distal and a proximal end of the housing, the presetting member being rotatable relative to the housing to set a maximum dose size, and the presetting member remaining rotatably disposed on the housing between the distal and proximal ends during presetting of the limit of the maximum dose size, which is accomplished by rotating the presetting member;
a first stopping member coupled to the presetting member, wherein rotation of the presetting member results in a change in position of the first stopping member such that a user can preset a maximum dose size;
a second stopping member that engages with the first stopping member and, when the first and second stopping members are engaged, the stopping members prevent rotation of the dose setting member in a direction that would allow the user to set a dose that is larger than the maximum preset dose which was set by the presetting member, and wherein a rotational force applied by and between the first and second stopping members as a result of their rotational abutment with each other during the setting of a dose via the dose setting member does not result in rotation of the presetting member and thus does not change the size of the maximum preset dose;
wherein the second stopping member is moveable along with the dose setting member during the setting of a dose, the movement causing the first and second stopping members to perform a rotational movement relative to each other, the relative rotational movement causing the first and second stopping members to engage when the maximum settable dose has been reached during dose setting via the dose setting member, the maximum settable dose being one set by rotating the presetting member, wherein the first and second members engage rotationally and not axially during dose setting when the dose setting member is rotated and wherein during dose setting the angular distance between the first and second stopping members decreases until they engage.

3. The device of claim 1 or claim 2, wherein the angular distance between the first and second stopping members increase during injection of a dose by rotating away from each other.

4. The device of claim 1 or claim 2, wherein the presetting member is adjustable after the setting of an initial dose by the dose setting member and wherein rotation of the presetting member after the setting of the initial dose results in rotational engagement, without axial abutment, of the first and second stopping members and wheiren after the first and second stopping members have been engaged by rotating the presetting member, the dose setting member is prevented further rotation in a direction that would increase dose size.

5. The device of claim 4, wherein following an injection that follows adjustment of the presetting member, the dose setting member is rotatable only up to the maximum preset dose size.

6. The device of claim 1 or 2, in combination with the pen apparatus, wherein the pen apparatus comprises a dose expelling mechanism.

* * * * *